(12) United States Patent
Mao et al.

(10) Patent No.: US 12,220,603 B2
(45) Date of Patent: Feb. 11, 2025

(54) HIGH-INTENSITY FOCUSED ULTRASOUND APPARATUS AND CONTROL METHOD

(71) Applicant: ULTRASOUND ASSISTED MEDTECH PTE. LTD., Guangdong (CN)

(72) Inventors: Jiawei Mao, Guangdong (CN); Jinqiang Yuan, Guangdong (CN); Zuping Jiang, Guangdong (CN); Jia Zhou, Guangdong (CN); Xiaobin Gao, Guangdong (CN)

(73) Assignee: ULTRASOUND ASSISTED MEDTECH PTE. LTD., Shenzhen (CN)

( * ) Notice: Subject to any disclaimer, the term of this patent is extended or adjusted under 35 U.S.C. 154(b) by 161 days.

(21) Appl. No.: 17/916,122

(22) PCT Filed: Mar. 12, 2021

(86) PCT No.: PCT/CN2021/080490
§ 371 (c)(1),
(2) Date: Sep. 30, 2022

(87) PCT Pub. No.: WO2021/203910
PCT Pub. Date: Oct. 14, 2021

(65) Prior Publication Data
US 2023/0330444 A1    Oct. 19, 2023

(30) Foreign Application Priority Data

Apr. 6, 2020    (SG) ............................ 10202003167Y
May 15, 2020   (CN) ......................... 202010412554.8

(51) Int. Cl.
*A61N 7/02* (2006.01)
*A61N 7/00* (2006.01)

(52) U.S. Cl.
CPC ...... *A61N 7/022* (2013.01); *A61N 2007/0052* (2013.01); *A61N 2007/0078* (2013.01)

(58) Field of Classification Search
None
See application file for complete search history.

(56) References Cited

U.S. PATENT DOCUMENTS

2003/0171701 A1    9/2003    Babaev
2004/0242999 A1*  12/2004    Vitek ................. A61B 17/2202
                                                                    600/437

(Continued)

FOREIGN PATENT DOCUMENTS

CN        1338909 A        3/2002

OTHER PUBLICATIONS

International Search Report of PCT Patent Application No. PCT/CN2021/080490 issued on May 28, 2021.

*Primary Examiner* — Katherine L Fernandez

(57) ABSTRACT

Provided are a high-intensity focused ultrasound apparatus (10) and a control method. According to the high-intensity focused ultrasound apparatus (10), by providing a focusing transducer (120) having a freely transformable shape, after an entire transducer assembly (100) extends into an inner cavity of an object to be treated, the transducer assembly (100) can extend through a narrow part into the inner cavity of an object to be treated, and after extending into the inner cavity of the object to be treated, the shape of the focusing transducer (120) in the transducer assembly (100) changes, so that the effective area of the focusing transducer (120) increases, and the ultrasonic energy produced increases, thereby enhancing the irradiation intensity for a region to be treated, and satisfying normal operation requirements of the transducer assembly (100).

1 Claim, 10 Drawing Sheets

(56) References Cited

U.S. PATENT DOCUMENTS

| | | | |
|---|---|---|---|
| 2009/0088636 A1* | 4/2009 | Lau | A61N 7/022 600/439 |
| 2014/0005521 A1* | 1/2014 | Kohler | A61B 6/4057 601/3 |
| 2019/0053821 A1* | 2/2019 | Rem-Bronneberg | A61B 17/320068 |
| 2021/0353253 A1* | 11/2021 | Da Cruz | A61B 8/445 |

* cited by examiner

HIGH-INTENSITY FOCUSED ULTRASOUND APPARATUS AND CONTROL METHOD

FIELD OF THE INVENTION

The present application relates to the technical field of medical devices, in particular to a high-intensity focused ultrasound apparatus and a control method.

BACKGROUND OF THE INVENTION

High-intensity focused ultrasound (HIFU) has become a popular research area in recent years in the field of ultrasonic treatment due to the characteristics of non-invasiveness and strong focusing. There are currently two action mechanisms of high-intensity focused ultrasound: a thermal ablation mechanism and a histotripsy mechanism. The thermal ablation mechanism mainly uses the thermal effect of ultrasound to focus ultrasonic energy to a target region, forming localized high-intensity ultrasonic energy to ablate tissue in the target region, so that the tissue in the target region is instantly in a high-temperature environment, resulting in coagulative necrosis. The histotripsy mode mainly uses the cavitation mechanical effect of HIFU to shatter tissues in a target region into micron-sized fragments.

However, in conventional solutions, due to limitations of equipment cost and technical difficulty, ultrasonic energy for releasing high-intensity focused ultrasonic pulses is emitted by an ultrasonic energy source arranged in vitro, and it is difficult to arrange the ultrasonic energy source in vivo, resulting in the problem of lack of detecting heads or probes for in vivo high-intensity focused ultrasound treatment in conventional solutions.

SUMMARY OF THE INVENTION

Based on this, it is necessary to provide a high-intensity focused ultrasound apparatus and a control method in view of the problem of lack of detecting heads or probes for in vivo high-intensity focused ultrasound treatment in conventional solutions.

The present application provides a high-intensity focused ultrasound apparatus, applied to an inner cavity of an object to be treated, comprising a transducer assembly and a connecting wire that are fixedly connected to each other, the connecting wire comprising a connecting end, the connecting wire being fixedly connected to the transducer assembly by means of the connecting end, the transducer assembly comprising:

an image transducer configured to acquire an ultrasound image of the inner cavity of the object to be treated; and a focusing transducer configured in a first shape, the focusing transducer being capable of freely changing to a second shape after extending into the inner cavity of the object to be treated, and configured to focus ultrasonic energy and release a high-intensity focused ultrasonic pulse to irradiate a region to be treated of the inner cavity of the object to be treated.

According to the high-intensity focused ultrasound apparatus in the present application, by providing the focusing transducer having a freely transformable shape, after the entire transducer assembly extends into the inner cavity of the object to be treated, not only can the transducer assembly extend through a narrow part into the inner cavity of the object to be treated, but also the shape of the focusing transducer in the transducer assembly changes after extension into the inner cavity of the object to be treated, so that the effective area of the focusing transducer increases, and the ultrasonic energy produced increases, thereby enhancing the irradiation intensity for the region to be treated, and satisfying normal operation requirements of the transducer assembly.

The present application also provides a control method of a high-intensity focused ultrasound apparatus, applied to the high-intensity focused ultrasound apparatus mentioned above, comprising:

sending an extending command to the transducer assembly to control the transducer assembly in the first shape to extend into the inner cavity of the object to be treated;

sending a shape change command to the focusing transducer in the transducer assembly to control the focusing transducer to perform a shape change from the first shape to the second shape;

setting a length of time of one operating cycle t and a number n of regions to be treated in one operating cycle t, where n is a positive integer and n is greater than 0;

sending an operating command to the focusing transducer to control the focusing transducer to perform an ultrasonic pulse treatment successively on the n regions to be treated in one operating cycle t; and repeatedly performing the step of sending an operating command to the focusing transducer to control the focusing transducer to accomplish ultrasonic pulse treatments on the n regions to be treated within a total operating cycle T, the total operating cycle T comprising M operating cycles t, where M is a positive integer and M is greater than 0.

According to the control method of a high-intensity focused ultrasound apparatus in the present application, by controlling the focusing transducer in the transducer to perform a shape change after the transducer assembly extends into the inner cavity of the object to be treated, not only can the transducer assembly extend through a narrow part into the inner cavity of the object to be treated, but also normal operation requirements of the transducer assembly are satisfied after extension into the inner cavity of the object to be treated. In addition, by controlling the focusing transducer to perform an ultrasonic pulse treatment successively on the plurality of regions to be treated in one operating cycle, the treatment time of ultrasonic pulse treatment is saved and the treatment efficiency is greatly improved.

REFERENCE NUMERALS

Figure 1:
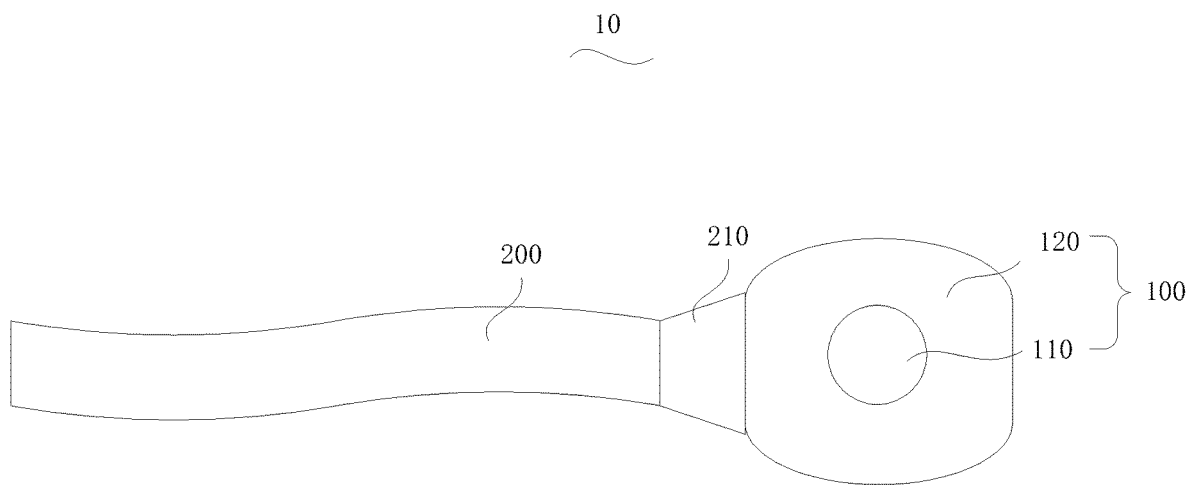
FIG. 1 is a schematic structural diagram of a high-intensity focused ultrasound apparatus provided in an embodiment of the present application.

10 High-intensity focused ultrasound apparatus
100 Transducer assembly
110 Image transducer
120 focusing transducer
121 Recess
122 First transducer module
122*a* Depression
123 Second transducer module
124 Third transducer module
125 Fourth transducer module
126 Fifth transducer module
126*a* Fifth transducer module a
126*b* Fifth transducer module b
126*c* Fifth transducer module c
130 Movable pin
200 Connecting wire
210 Connecting end
300 Control wire
310 First control wire
320 Second control wire

DETAILED DESCRIPTION OF THE EMBODIMENTS

To make the objectives, technical solutions and advantages of the present application clearer and more apparent, the present application will be further described in detail below in conjunction with the accompanying drawings and embodiments. It should be appreciated that the specific embodiments described herein are only intended to explain the present application, and are not used for limiting the present application.

The present application provides a high-intensity focused ultrasound apparatus 10 applied to an inner cavity of an object to be treated.

As shown in FIG. 1, in an embodiment of the present application, the high-intensity focused ultrasound apparatus 10 includes a transducer assembly 100 and a connecting wire 200 that are fixedly connected to each other. The connecting wire 200 includes a connecting end 210. The connecting wire 200 is fixedly connected to the transducer assembly 100 by means of the connecting end 210. The transducer assembly 100 includes an image transducer 110 and a focusing transducer 120. The image transducer 110 is configured to acquire an ultrasonic image of the inner cavity of the object to be treated. The focusing transducer 120 is configured in a first shape. The focusing transducer 120 can freely change to a second shape after extending into the inner cavity of the object to be treated. The focusing transducer 120 is configured to focus ultrasonic energy and release a high-intensity focused ultrasonic pulse to irradiate a region to be treated of the inner cavity of the object to be treated.

Specifically, the inner cavity of the object to be treated may be the stomach, the rectum, or the like. When the high-intensity focused ultrasound apparatus 10 is outside the object to be treated, the focusing transducer 120 is in the first shape, which is configured for easy entry into the inner cavity of the object to be treated. It may be appreciated that organs such as the stomach or the rectum have relatively narrow entrances, which the focusing transducer 120 in the first shape can easily enter. When the high-intensity focused ultrasound apparatus 10 is in the inner cavity of the object to be treated, the focusing transducer 120 is in the second shape, which increases the effective area of the focusing transducer 120. It may be appreciated that the larger the effective area of the focusing transducer 120, the more ultrasonic energy is produced and the higher the irradiation intensity to irradiate the region to be treated of the inner cavity of the object to be treated.

The high-intensity focused ultrasound apparatus 10 may be electrically connected to an upper computer. Specifically, the upper computer is electrically connected to the connecting wire 200 to control shape changes of the focusing transducer 120. Specifically, the upper computer may include one or more processors, which are configured to control shape changes of the focusing transducer 120.

In this embodiment, by providing the focusing transducer 120 having a freely transformable shape, after the entire transducer assembly 100 extends into the inner cavity of the object to be treated, not only can the transducer assembly 100 extend through a narrow part into the inner cavity of the object to be treated, but also the shape of the focusing transducer 120 in the transducer assembly 100 changes after extension into the inner cavity of the object to be treated, so that the effective area of the focusing transducer 120 increases, and the ultrasonic energy produced increases, thereby enhancing the irradiation intensity for the region to be treated, and satisfying normal operation requirements of the transducer assembly 100.

Embodiment 1

Figure 2:
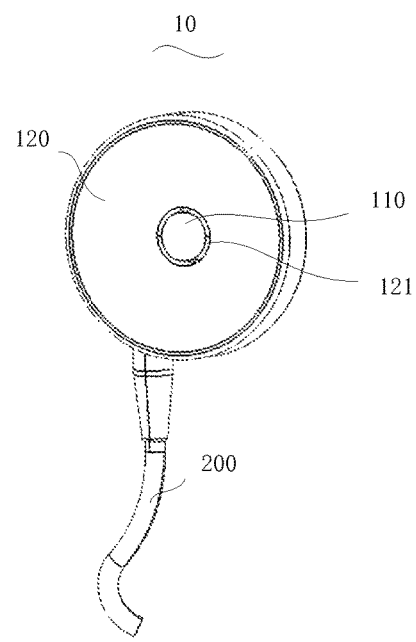
FIG. 2 is a three-dimensional structural diagram of the high-intensity focused ultrasound apparatus when a focusing transducer is in a second shape in Embodiment 1 of the present application.

As shown in FIG. 2, in an embodiment of the present application, the second shape is a circular cylinder or an elliptic cylinder. At least one end face of the circular cylinder or elliptic cylinder is a concave spherical surface. The focusing transducer 120 has a recess 121.

The image transducer 110 is in the shape of a circular cylinder or an elliptic cylinder. The image transducer 110 is embedded in the recess 121. A circle center of an end face of the image transducer 110 coincides with a physical center of an end face of the focusing transducer 120.

Specifically, in Embodiment 1, the second shape of the focusing transducer 120 is a circular cylinder or an elliptic cylinder, i.e., the focusing transducer 120 is in an unfolded shape in the inner cavity of the object to be treated. The difference is that in the case the second shape is a circular cylinder, the two end faces are round; and in the case the second shape is an elliptic cylinder, the two end faces are elliptic. At least one end face of the circular cylinder or elliptic cylinder is configured as a concave spherical surface, which enables the focusing transducer 120 to better focus the ultrasonic energy. The focusing transducer 120 can focus ultrasonic energy at the physical center of the end face of the focusing transducer 120. The image transducer 110 is provided so that the transducer assembly 100 not only has the function of releasing a high-intensity focused ultrasonic pulse, but also has the function of acquiring an ultrasonic image of the treated object. FIG. 2 shows a schematic diagram of an embodiment in which the second shape is a circular cylinder and one end face of the circular cylinder is configured as a concave spherical surface.

In this embodiment, by providing the image transducer 110 embedded in the recess 121 of the focusing transducer 120, the transducer assembly 100 not only has the function of releasing a high-intensity focused ultrasonic pulse, but also has the function of acquiring an ultrasonic image of the treated object.

Embodiment 1 has different forms of extended embodiments, and two extended embodiments are listed below: Embodiment 1-1 and Embodiment 1-2. In the two extended embodiments, the first shape of the focusing transducer 120 is different, and the second shape of the focusing transducer 120 is the same.

Embodiment 1-1

Figure 3:
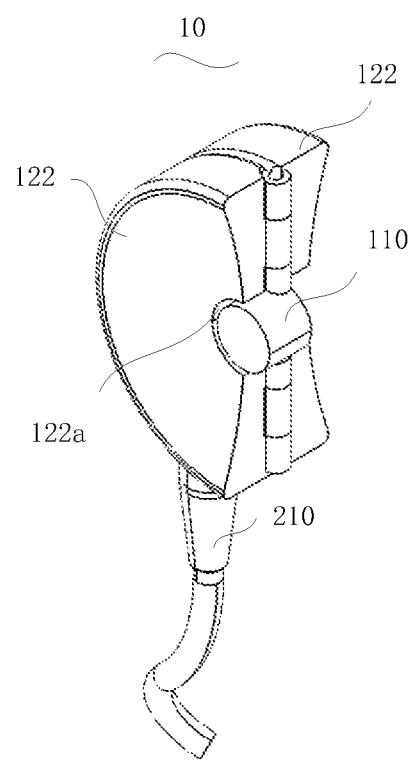
FIG. 3 is a three-dimensional structural diagram of the high-intensity focused ultrasound apparatus when a focusing transducer is in a first shape in Embodiment 1-1 of the present application.
Figure 4:
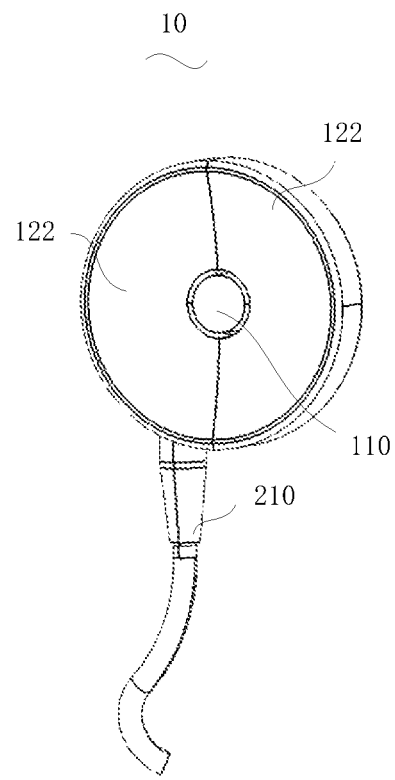
FIG. 4 is a three-dimensional structural diagram of the high-intensity focused ultrasound apparatus when the focusing transducer is in a second shape in Embodiment 1-1 of the present application.

As shown in FIGS. 3 and 4, in an embodiment of the present application, the focusing transducer 120 comprises two first transducer modules 122. In the case the second shape is a circular cylinder, each of the first transducer modules 122 is in the shape of a semi-circular cylinder formed after the circular cylinder as the second shape is separated by an axial cross-section. In the case the second shape is an elliptic cylinder, each of the first transducer modules 122 is in the shape of a semi-elliptic cylinder formed after the elliptic cylinder as the second shape is separated by an axial cross-section. The first transducer module 122 has a depression 122a.

When the high-intensity focused ultrasound apparatus 10 is in a first state, the two first transducer modules 122 are folded and combined to form the focusing transducer 120 in the first shape. The first shape is a semi-circular cylinder formed by folding the two semi-circular cylinders or a semi-elliptic cylinder formed by folding the two semi-elliptic cylinders The first state is that the high-intensity focused ultrasound apparatus 10 is outside the object to be treated.

When the high-intensity focused ultrasound apparatus 10 is in a second state, the two first transducer modules 122 are unfolded and spliced to form the focusing transducer 120 in the second shape. The depressions 122a of the two first transducer modules 122 are spliced to form the recess 121. The second state is that the high-intensity focused ultrasound apparatus 10 is in the inner cavity of the object to be treated. During a shape change of the focusing transducer 120, the shape and the position of the image transducer 110 remain unchanged.

Specifically, the focusing transducer 120 in this embodiment can be applied to the rectum. It is to be note that the first state is that the high-intensity focused ultrasound apparatus 10 is outside the object to be treated. The second state is that the high-intensity focused ultrasound apparatus 10 is in the inner cavity of the object to be treated. The first state and the second state appearing hereinafter have the same meanings, which will not be repeated. The focusing transducer 120 includes two semi-circular-cylinder or two semi-elliptic-cylinder first transducer modules 122. The focusing transducer 120 shown in FIGS. 3 and 4 includes two semi-circular-cylinder first transducer modules 122. With this as an example for explanation, the inner cavity of the object to be treated is the rectum, for example, an entrance of which is relatively narrow, and the two first transducer modules 122 of the focusing transducer 120 are folded to form a semi-circular-cylinder structure, to extend into the rectum. Upon entering the interior of the rectum, the two semi-circular-cylinder first transducer modules 122 are unfolded and spliced to form a complete circular cylinder to facilitate subsequent release of a high-intensity focused ultrasonic pulse for irradiation of the region to be treated.

In Embodiment 1-1, a biasing connector (not shown in the figures) may be provided between the two first transducer modules 122. The biasing connector may be a spring. When the high-intensity focused ultrasound apparatus 10 is in the first state, the upper computer can control the biasing connector to maintain the focusing transducer 120 in the first shape. A mechanical transmission mechanism may also be provided between the first transducer modules 122. The mechanical transmission mechanism is mechanically connected to the biasing connector. When the high-intensity focused ultrasound apparatus 10 is in the first state, the upper computer can control the mechanical transmission mechanism to drive the biasing connector to change its bias state, such that the focusing transducer 120 changes its shape to the second shape.

In this embodiment, by providing the two semi-circular-cylinder or two semi-elliptic-cylinder first transducer modules 122, when the high-intensity focused ultrasound apparatus 10 is outside the object to be treated, the modules can be folded for easy entry into the inner cavity of the object to be treated; and when the high-intensity focused ultrasound apparatus 10 is in the inner cavity of the object to be treated, the modules can be unfolded and spliced to form a complete circular cylinder or a complete elliptic cylinder, which increases the effective area of the focusing transducer 120, so the overall structure of the focusing transducer 120 is simple.

Embodiment 1-2

Figure 5:
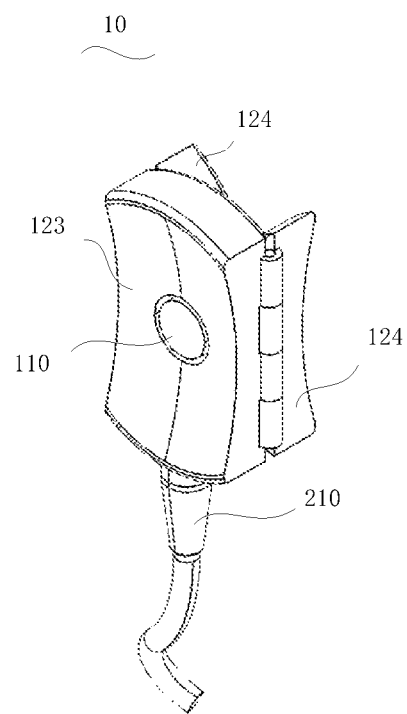
FIG. 5 is a three-dimensional structural diagram of the high-intensity focused ultrasound apparatus when a focusing transducer is in a first shape in Embodiment 1-2 of the present application.
Figure 6:
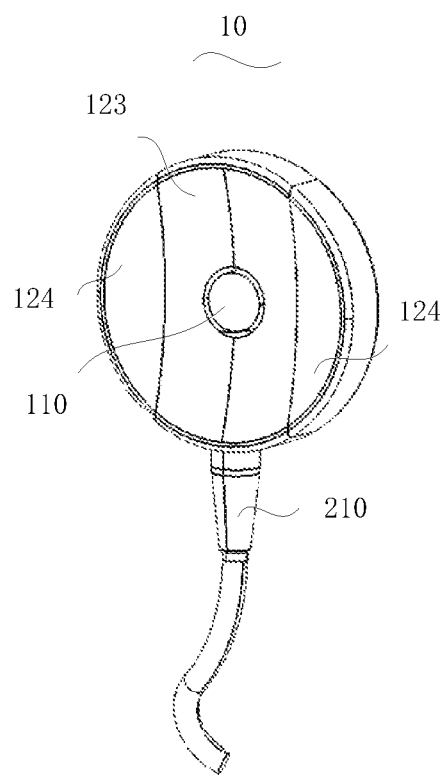
FIG. 6 is a three-dimensional structural diagram of the high-intensity focused ultrasound apparatus when the focusing transducer is in a second shape in Embodiment 1-2 of the present application.

As shown in FIGS. 5 and 6, in an embodiment of the present application, the focusing transducer 120 includes a second transducer module 123 and two third transducer modules 124. The two third transducer modules 124 are arranged on two sides of the second transducer module 123, respectively. The two third transducer modules 124 are respectively movably connected to the second transducer module 123. The recess 121 is provided in the second transducer module 123.

When the high-intensity focused ultrasound apparatus 10 is in the first state, the two third transducer modules 124 are folded and combined to form the focusing transducer 120 in the first shape. The first state is that the high-intensity focused ultrasound apparatus 10 is outside the object to be treated. The first shape is the shape of the second transducer module 123.

When the high-intensity focused ultrasound apparatus 10 is in the second state, the two third transducer modules 124 are unfold and spliced to form the focusing transducer 120 in the second shape. The second state is that the high-intensity focused ultrasound apparatus 10 is in the inner cavity of the object to be treated. The image transducer 110 is embedded in the recess 121. During a shape change of the focusing transducer 120, the shapes and the positions of the second transducer module 123 and the image transducer 110 remain unchanged.

Specifically, in Embodiment 1-1, the circular-cylinder focusing transducer 120 is divided into two semi-cylinders. In Embodiment 1-2, the cylindrical focusing transducer 120 is divided into three sequentially adjacent parts: a second transducer module 123 and two third transducer modules 124. The two third transducer modules 124 are arranged on two sides of the second transducer module 123, respectively, and are movably connected to the second transducer module 123. The third transducer module 124 may be a half-moon structure. When the high-intensity focused ultrasound apparatus 10 is in the first state, the two third transducer modules 124 are folded, and the focusing transducer 120 is in the first shape to facilitate entering the inner cavity of the object to be treated. When the high-intensity focused ultrasound apparatus 10 is in the second state, the two third transducer modules 124 are unfolded and are spliced with the second transducer module 123 into the second shape, such that the effective area of the focusing transducer increases.

In Embodiment 1-2, a biasing connector and a mechanical transmission mechanism (not shown in the figures) may be provided between the second transducer module 123 and the third transducer modules 124. The mechanical transmission mechanism is mechanically connected to the biasing connector. The biasing connector may be a spring. When the high-intensity focused ultrasound apparatus 10 is in the first state, the upper computer can control the biasing connector to maintain the focusing transducer 120 in the first shape. When the high-intensity focused ultrasound apparatus 10 is in the first state, the upper computer can control the mechanical transmission mechanism to drive the biasing connector to change its bias state, such that the focusing transducer 120 changes its shape to the second shape.

In this embodiment, by providing the second transducer module 123 and the two third transducer modules 124 located on the two sides of the second transducer module 123, when the high-intensity focused ultrasound apparatus 10 is outside the object to be treated, the modules can be folded for easy entry into the inner cavity of the object to be treated; and when the high-intensity focused ultrasound apparatus 10 is in the inner cavity of the object to be treated, the modules can be unfolded and spliced to form a complete circular cylinder, which increases the effective area of the focusing transducer 120, so the overall structure of the focusing transducer 120 is simple.

Embodiment 2

Figure 7:
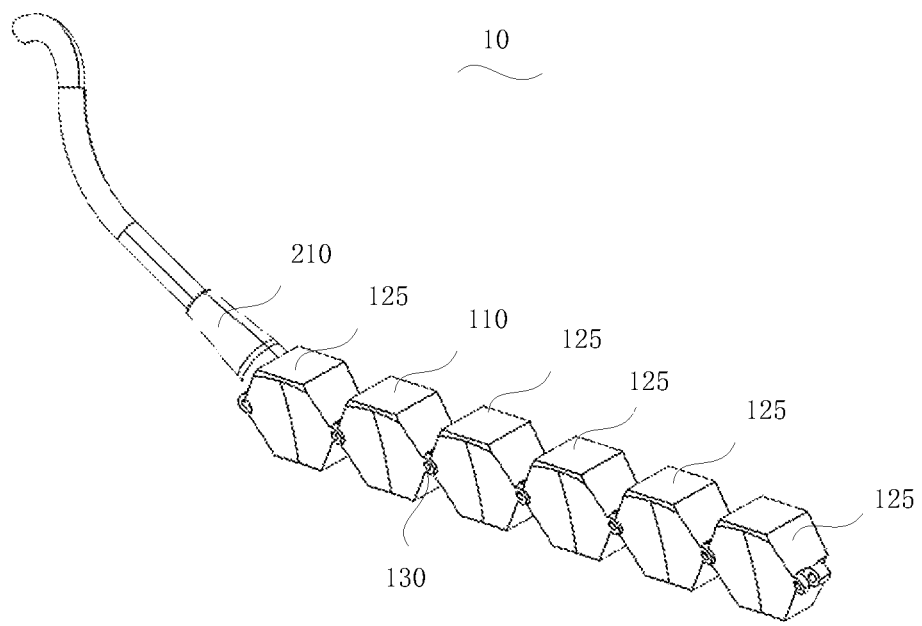
FIG. 7 is a three-dimensional structural diagram of the high-intensity focused ultrasound apparatus when a focusing transducer is in a first shape in Embodiment 2 of the present application.
Figure 8:
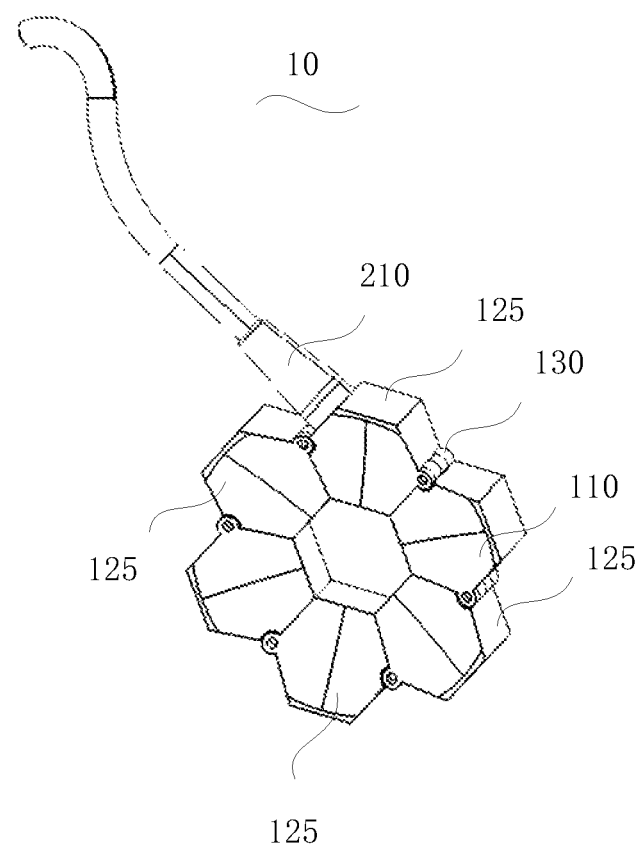
FIG. 8 is a three-dimensional structural diagram of the high-intensity focused ultrasound apparatus when a focusing transducer is in a second shape in Embodiment 2 of the present application.

As shown in FIGS. 7 and 8, in an embodiment of the present application, the first shape is a chain structure consisting of a plurality of regular hexagonal prisms, which are connected successively. The second shape is an annular structure consisting of the plurality of regular hexagonal prism, of which the first is connected to the last to form an enclosure in the same plane.

Specifically, Embodiment 2 differs from Embodiment 1. In Embodiment 2, the first shape is a chain structure for easy extension into the entrance of the narrow inner cavity of the object to be treated, e.g., the entrance of the rectum. The regular hexagonal prism has two regular hexagonal surfaces. In the chain structure, the regular hexagonal surfaces of the plurality of regular hexagonal prisms are located in the same plane. After entering the inner cavity of the object to be treated, the plurality of regular hexagonal prisms form the annular structure in such a manner that the first is connected to the last to form an enclosure, which increases the effective area of the focusing transducer 120. In addition, the second shape formed is a regular shape, allowing the ultrasonic energy to be focused at one point, with energy focus points being located in a physical center of the annular structure. When the focusing transducer 120 is in the first shape, its energy focus points are dispersed. When the focusing transducer 120 is in the second shape, its energy focus points overlap, allowing the ultrasonic energy to be focused at one point.

In this embodiment, by designing the first shape of the chain structure and the second shape of the annular structure, after the focusing transducer 120 extends into the inner cavity of the object to be treated, the effective area of the focusing transducer 120 can be increased and the ultrasonic energy can be focused at one point.

Still referring to FIGS. 7 and 8, in an embodiment of the present application, the focusing transducer 120 includes a plurality of fourth transducer modules 125 connected successively by movable pins 130. Each of the fourth transducer modules 125 is in the shape of a regular hexagonal prism. The image transducer 110 is in the shape of a regular hexagonal prism. The image transducer 110 is arranged at an end of the chain structure or between two fourth transducer modules 125 when the focusing transducer 120 is the chain structure in the first shape.

When the high-intensity focused ultrasound apparatus 10 is in a first state, the plurality of fourth transducer modules 125 are unfolded and combined to form the focusing transducer 120 in the first shape. The first state is that the high-intensity focused ultrasound apparatus 10 is outside the object to be treated.

When the high-intensity focused ultrasound apparatus 10 is in a second state, the fourth transducer module 125 farthest from the connecting end 210 approaches the fourth transducer module 125 closest to the connecting end 210, so that the plurality of fourth transducer modules 125 form, by enclosure, the focusing transducer 120 in the second shape. The second state is that the high-intensity focused ultrasound apparatus 10 is in the inner cavity of the object to be treated.

Specifically, a biasing connector and a mechanical transmission mechanism may be provided between two adjacent fourth transducer modules 125. The mechanical transmission mechanism is mechanically connected to the biasing connector. The biasing connector may be a spring. When the high-intensity focused ultrasound apparatus 10 is in the first state, the upper computer can control the biasing connector to maintain the focusing transducer 120 in the first shape. When the high-intensity focused ultrasound apparatus 10 is in the first state, the upper computer can control the mechanical transmission mechanism to drive the biasing connector to change its bias state, such that the focusing transducer 120 changes its shape to the second shape.

The image transducer 110 is arranged at an end of the chain structure, i.e. the image transducer 110 may be the regular hexagonal prism closest to the connecting end 210 or the regular hexagonal prism farthest from the connecting end 210. The image transducer 110 may also be arrange between two fourth transducer modules 125.

When the focusing transducer 120 is in the first shape, its energy focus points are dispersed. When the focusing transducer 120 is in the second shape, its energy focus points overlap, allowing the ultrasonic energy to be focused at one point.

In this embodiment, by providing the plurality of fourth transducer modules 125 connected successively by the movable pins 130 to form the chain structure, after the focusing transducer 120 extends into the inner cavity of the object to be treated, the fourth transducer module 125 farthest from the connecting end 210 approaches the fourth transducer module 125 closest to the connecting end 210 to form, by enclosure, the annular structure, which not only can increase the effective area of the focusing transducer 120, but also allows the ultrasonic energy to be focused at one point.

In Embodiment 2, the focusing transducer 120 of the chain structure is transformed into the annular structure in which the first is connected to the last. The specific way of transformation depends on a driving structure of the focusing transducer 120 itself, and 2 embodiments using different driving structures are described below.

Embodiment 2-1

Figure 9:
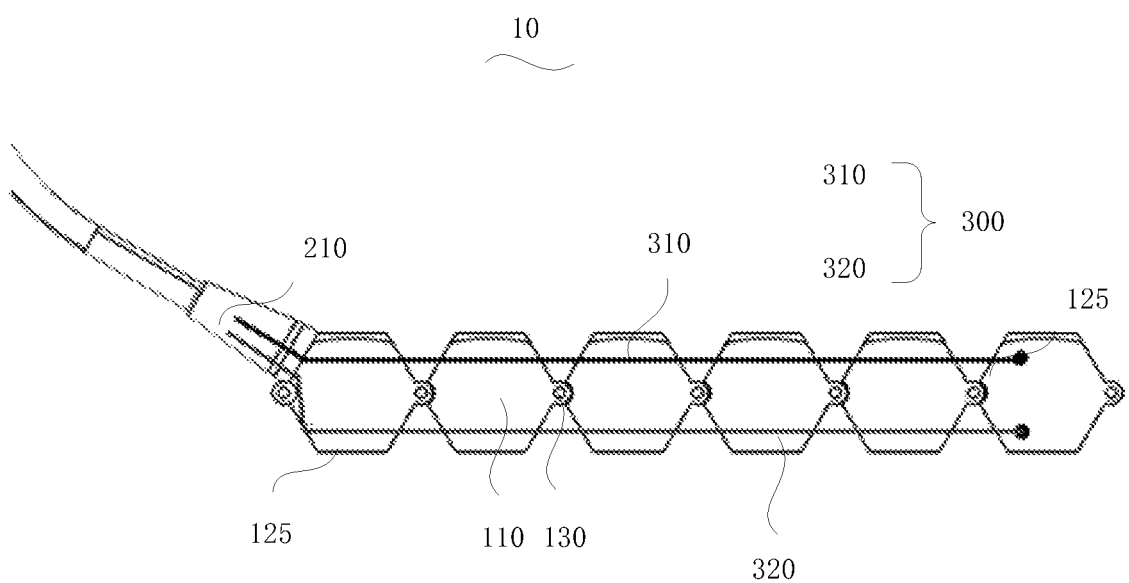
FIG. 9 is a three-dimensional structural diagram of the high-intensity focused ultrasound apparatus when a focusing transducer provided in Embodiment 2-1 of the present application is in a first shape.

As shown in FIG. 9, in an embodiment of the present application, the high-intensity focused ultrasound apparatus 10 further includes two control wires 300 running through each of the fourth transducer modules 125. The two control wires 300 do not cross each other. When the high-intensity focused ultrasound apparatus 10 is in the first state, the two control wires 300 are relaxed simultaneously to achieve that the plurality of fourth transducer modules 125 form, by unfolding, the focusing transducer 120 in the first shape. When the high-intensity focused ultrasound apparatus 10 is in the second state, one control wire 300 is tensioned and the other control wire 300 is relaxed to achieve that the plurality of fourth transducer modules 125 form, by enclosure, the focusing transducer 120 in the second shape.

Specifically, in this embodiment, the control wires 300 are provided in the focusing transducer 120 to drive the focusing transducer 120 to change its shape. Specifically, as shown in FIG. 9, two control wires 300 may be included: a first control wire 310 and a second control wire 320. The first control wire 310 and the second control wire 320 do not cross each other. The first control wire 310 and the second control wire 320 both run through each of the fourth transducer modules 125. Since the plurality of fourth transducer modules 125 and the image transducer 110 together form the chain structure, the first control wire 310 and the second control wire 320 also run through the image transducer 110. In other words, the first control wire 310 and the second control wire 320 run through each of the regular hexagonal prisms in the chain structure.

As shown in FIG. 9, when the first control wire 310 and the second control wire 320 are relaxed simultaneously, the plurality of fourth transducer modules 125 are unfolded to form the first shape, i.e., the chain structure.

There are two wire control modes for forming the second shape.

1) When the first control wire 310 is relaxed and the second control wire 320 is tensioned, the fourth transducer module 125 farthest from the connecting end 210 is bent downward and the plurality of fourth transducer modules 125 are curled into an enclosure to form the second shape.

2) When the first control wire 310 is tensioned and the second control wire 320 is relaxed, the fourth transducer module 125 farthest from the connecting end 210 is bent upward and the plurality of fourth transducer modules 125 are curled into an enclosure to form the second shape.

The two wire control modes for the first control wire 310 and the second control wire 320 can both implement the formation of the second shape by the plurality of fourth transducer modules 125.

In this embodiment, by providing the two control wires 300, a shape change of the chain structure consisting of the plurality of fourth transducer modules 125 and the image transducer 110 can be implemented during the traction and/or relaxation of the control wires. The operation is simple and the cost is low.

Embodiment 2-2

In an embodiment of the present application, the fourth transducer module 125 closest to the connecting end 210 is a magnet. The fourth transducer module 125 farthest from the connecting end 210 is a magnet.

When the high-intensity focused ultrasound apparatus 10 is in the second state, the fourth transducer module 125 farthest from the connecting end 210 is controlled to come into close proximity to the fourth transducer module 125 closest to the connecting end 210, to achieve that the fourth transducer module 125 farthest from the connecting end 210 and the fourth transducer module 125 closest to the connecting end 210 are attracted together, such that the plurality of fourth transducer modules 125 form, by enclosure, the focusing transducer 120 in the second shape.

Specifically, in this embodiment, magnetic attraction is used to drive the focusing transducer 120 to change its shape. Two fourth transducer modules 125 may be configured as magnets: one is the fourth transducer module 125 closest to the connecting end 210, and the other is the fourth transducer module 125 farthest from the connecting end 210. Of course, it is also possible that any one of the two fourth transducer modules 125 described above is configured as a magnet and the other is made of one of the materials of iron alloy, cobalt alloy and nickel alloy. The two magnets can be controlled to approach each other to achieve that the first and the last regular hexagonal prisms of the chain structure are attracted together to form, by enclosure, the second shape.

In this embodiment, by providing the fourth transducer module 125 closest to the connecting end 210 as a magnet, and the fourth transducer module 125 farthest from the connecting end 210 as a magnet, when the two magnets approach each other, the first and the last regular hexagonal prisms of the focusing transducer 120 of the chain structure are attracted together to form, by enclosure, the second shape. The shape change is fast.

Embodiment 3

Figure 10:
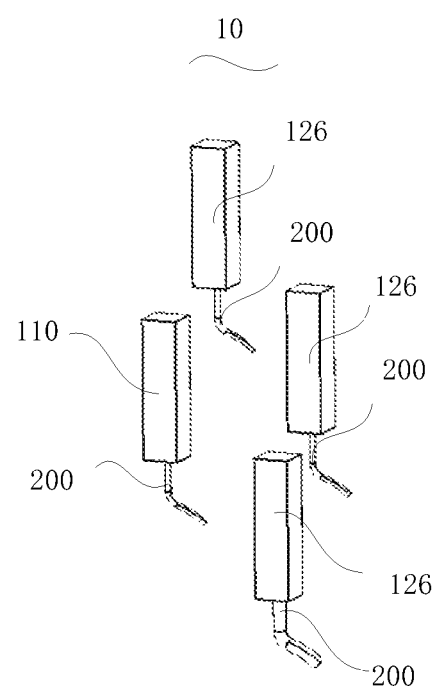
FIG. 10 is a three-dimensional structural diagram of the high-intensity focused ultrasound apparatus when a focusing transducer provided in Embodiment 3 of the present application is in a first shape.
Figure 11:
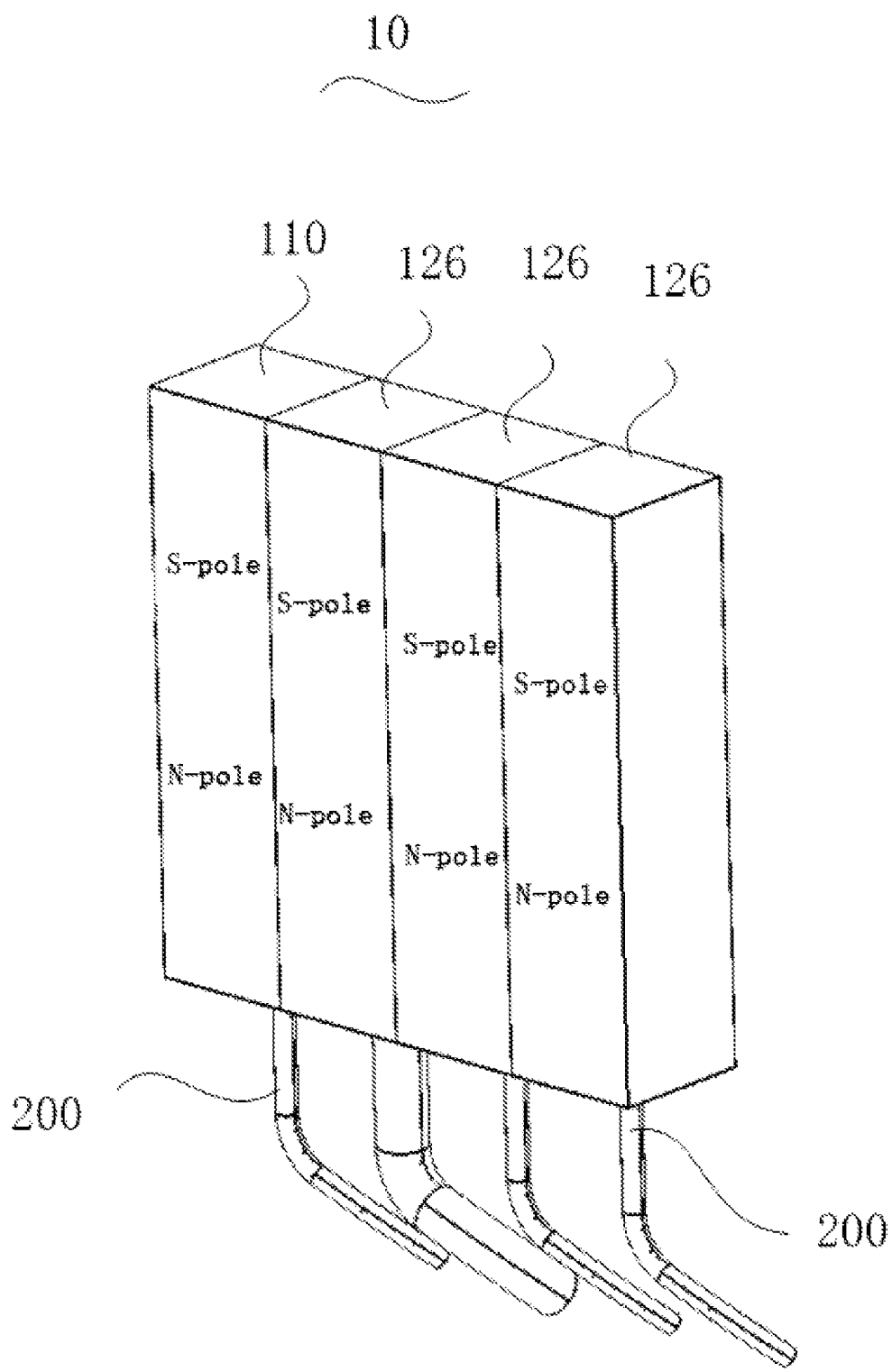
FIG. 11 is a three-dimensional structural diagram of the high-intensity focused ultrasound apparatus when the focusing transducer provided in Embodiment 3 of the present application is in a second shape.

As shown in FIGS. 10 and 11, in an embodiment of the present application, the focusing transducer 120 includes a plurality of fifth transducer modules 126. Pluralities of connecting wires 200 are provided. Each of the fifth transducer modules 126 is fixedly connected to one connecting wire 200. The image transducer 110 is fixedly connected to one connecting wire 200.

Specifically, the focusing transducer 120 in Embodiment 3 is equivalent to being dispersed into a plurality of fifth transducer modules 126, each fifth transducer module 126 existing independently, and each fifth transducer module 126 being fixedly connected to one connecting wire 200. It may be appreciated that the shape of each fifth transducer module 126 is the first shape. When the plurality of fifth transducer modules 126 successively extend into the inner cavity of the object to be treated, the plurality of fifth transducer modules 126 are combined to form the focusing transducer 120 of the second shape. There is an intensity threshold for an ultrasonic pulse that the object to be treated can withstand, and if a released high-intensity focused ultrasonic pulse is too strong, the object to be treated cannot withstand it. For example, intensity thresholds for ultrasonic pulses that the stomach and the rectum can withstand are different. In this embodiment, the number of the fifth transducer modules 126 can be adjusted according to different objects to be treated, to meet the pulse irradiation requirements of different objects to be treated. The focusing transducer 120 in this embodiment can be applied to different types of objects to be treated, such as the stomach, the rectum, etc.

In this embodiment, by providing the plurality of independent fifth transducer modules 126, the number of the fifth transducer modules 126 can be adjusted in real time according to different objects to be treated, to meet the pulse irradiation requirements of different objects to be treated, so that the high-intensity focused ultrasound apparatus 10 is not limited by a fixed type of object, thus saving the equipment cost and improving the operating efficiency.

Still referring to FIGS. 10 and 11, in an embodiment of the present application, the first shape is a cuboid. The second shape is a cuboid, and the fifth transducer modules 126 are magnets. The image transducer 110 is in the shape of a cuboid. The image transducer 110 is a magnet.

When the high-intensity focused ultrasound apparatus 10 is in the first state, the plurality of fifth transducer modules 126 are each independent. The first state is that the high-intensity focused ultrasound apparatus 10 is outside the object to be treated.

When the high-intensity focused ultrasound apparatus 10 enters the inner cavity of the object to be treated, first the plurality of fifth transducer modules 126 successively enter, in sequence, the inner cavity of the object to be treated, and after the plurality of fifth transducer modules 126 have all entered the inner cavity of the object to be treated, the image transducer 110 enters the inner cavity of the object to be treated; or first the image transducer 110 enters the inner cavity of the object to be treated, and after the image transducer 110 has entered the inner cavity of the object to be treated, the plurality of fifth transducer modules 126 successively enter, in sequence, the inner cavity of the object to be treated.

When the high-intensity focused ultrasound apparatus 10 is in a second state, an N-pole of one fifth transducer module 126 and an S-pole of another fifth transducer module 126 are magnetically attracted to each other so that the plurality of fifth transducer modules 126 together form the focusing transducer 120 in the second shape. The second state is that the high-intensity focused ultrasound apparatus 10 is in the inner cavity of the object to be treated. The image transducer 110 and one fifth transducer module 126 are magnetically attracted to each other.

Specifically, the fifth transducer modules 126 are cuboid magnets. Each fifth transducer module 126 has an N pole and an S pole. When the high-intensity focused ultrasound apparatus 10 enters the inner cavity of the object to be treated, the plurality of fifth transducer modules 126 successively enter, in sequence, the inner cavity of the object to be treated. When the high-intensity focused ultrasound apparatus 10 is in the inner cavity of the object to be treated, the plurality of fifth transducer modules 126 are naturally attracted to each other to form the second shape. The second shape is also a cuboid. It may be appreciated that the surface area of surfaces with the largest areas in the cuboid corresponding to the second shape is much larger than the surface area of surfaces with the largest areas in the cuboid corresponding to the first shape, so the effective area of the focusing transducer 120 increases, and the ultrasonic energy produced increases. The entering sequence of the image transducer 110 may be not limited, so long as it does not interfere with the attraction together of the plurality of fifth transducer modules 126 into the second shape. It may be the first to enter the inner cavity of the object to be treated, and it may also be the last to enter the inner cavity of the object to be treated.

In this embodiment, by providing the plurality of fifth transducer modules 126 as magnets, when the high-intensity focused ultrasound apparatus 10 is in the inner cavity of the object to be treated, the plurality of fifth transducer modules 126 are naturally attracted to each other to form a cuboid shape with an increased effective area, so that the effective area of the focusing transducer 120 increases, the ultrasonic energy produced increases, and the number of fifth transducer modules can be increased or reduced according to different objects to be treated, which is flexible and convenient in the actual use and saves the use cost.

Figure 12:
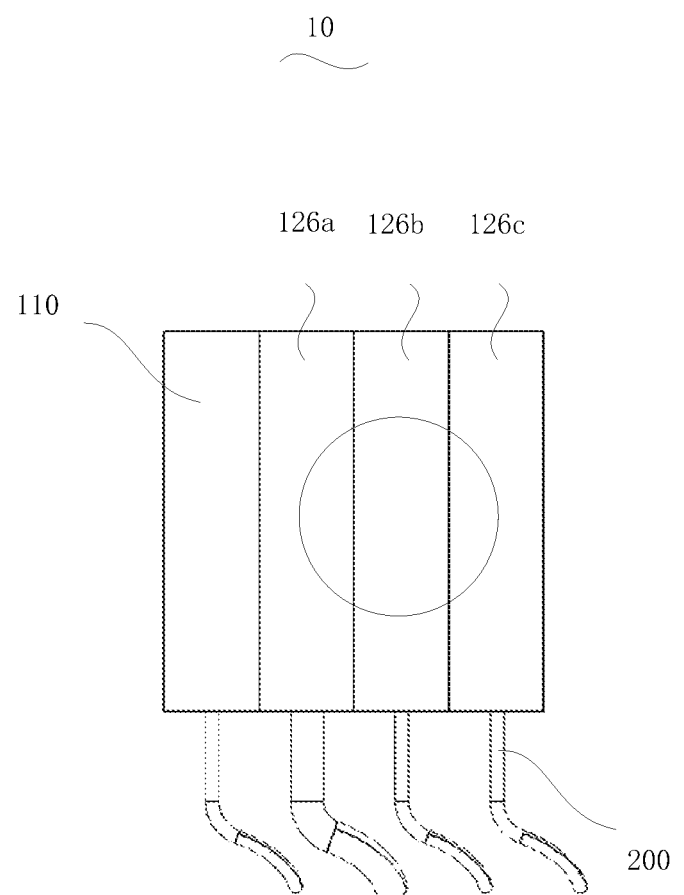
FIG. 12 is a front view of the high-intensity focused ultrasound apparatus when the focusing transducer provided in Embodiment 3 of the present application is in the second shape.

As shown in FIG. 12, in an embodiment of the present application, in the cuboid corresponding to the second shape, at least one of two faces with the largest areas is a concave spherical surface. A physical center of the concave spherical surface is where energy focus points of the focusing transducer 120 are located.

In the cuboid corresponding to the first shape, at least one of two faces with the largest areas is a concave surface. The concave surfaces of a plurality of cuboids corresponding to the first shape form, by an ordered combination, the concave spherical surface of the cuboid corresponding to the second shape.

Specifically, as shown in FIG. 12, the shape of each fifth transducer module 126 is the first shape, with a face having the largest area being configured as a concave surface. In this embodiment, an ordered combination of the plurality of fifth transducers is required to enable the concave surfaces of the plurality of fifth transducer modules 126 to form, by a combination, the concave spherical surface of the cuboid corresponding to the second shape after the plurality of fifth transducer modules 126 are attracted together. The concave spherical surface allows the energy focus points to be fixed at one point, i.e. the physical center of the concave spherical surface, such that the ultrasonic energy produced by the focusing transducer 120 increases.

In this embodiment, by providing a surface with the largest area as a concave spherical surface, the energy focus points can be fixed at one point, i.e. the physical center of the concave spherical surface, such that the ultrasonic energy produced by the focusing transducer 120 increases.

In an embodiment of the present application, when the high-intensity focused ultrasound apparatus 10 enters the inner cavity of the object to be treated, the plurality of fifth transducer modules 126 successively enter, in a predetermined order, the inner cavity of the object to be treated, so that the concave surfaces of the plurality of cuboids corresponding to the first shape form, by an ordered combination, the concave spherical surface of the cuboid corresponding to the second shape.

Specifically, following the above embodiment, to enable the concave surfaces of the plurality of fifth transducer modules 126 to form, by a combination, the concave spherical surface of the cuboid corresponding to the second shape, the plurality of fifth transducer modules 126 need to successively enter, in a predetermined order, the inner cavity of the object to be treated. The predetermined order is preset artificially. For example, as shown in FIG. 12, the fifth transducer modules 126 include a fifth transducer module a, a fifth transducer module b, a fifth transducer module c, and a fifth transducer module d. The formation of the concave spherical surface of the cuboid corresponding to the second shape can be achieved by placing the plurality of fifth transducer modules 126 in a predetermined order of a-b-c-d into the inner cavity of the object to be treated.

In this embodiment, by setting the order in which the plurality of fifth transducer modules 126 are placed into the inner cavity of the object to be treated, the formation of the concave spherical surface of the cuboid corresponding to the second shape is achieved, so that the energy focus points are fixed at one point, i.e. the physical center of the concave spherical surface, such that the ultrasonic energy produced by the focusing transducer 120 increases.

The present application also provides a control method of a high-intensity focused ultrasound apparatus. The control method of a high-intensity focused ultrasound apparatus is applied to the high-intensity focused ultrasound apparatus 10 mentioned above.

It is to be noted that the application fields and application scenarios of the present application are not limited.

An executing device of the control method of a high-intensity focused ultrasound apparatus provided in the present application is not limited. Optionally, the executing device of the control method of a high-intensity focused ultrasound apparatus may be an upper computer connected to the high-intensity focused ultrasound apparatus 10. Optionally, the executing device of the control method of a high-intensity focused ultrasound apparatus may be one or more processors in the upper computer.

Figure 13:
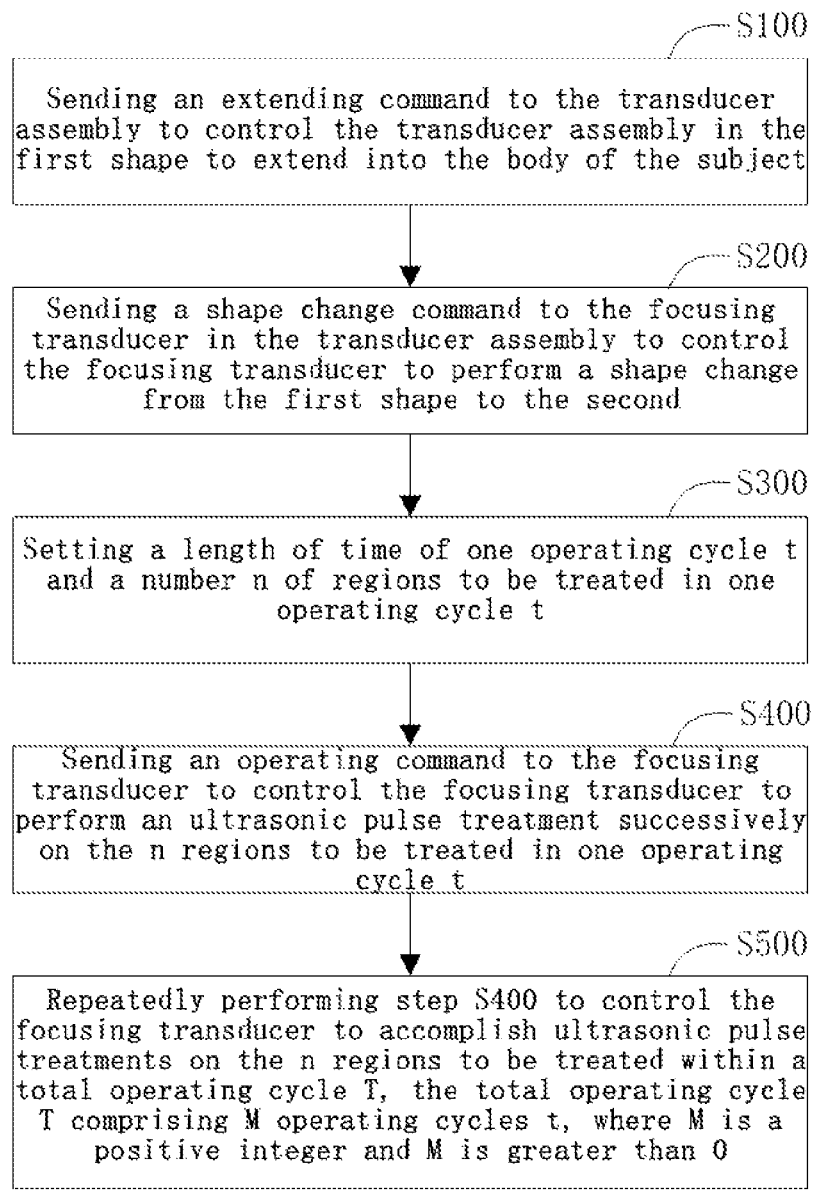
FIG. 13 is a schematic flow diagram of a control method of a high-intensity focused ultrasound apparatus provided in an embodiment of the present application.
Figure 14:
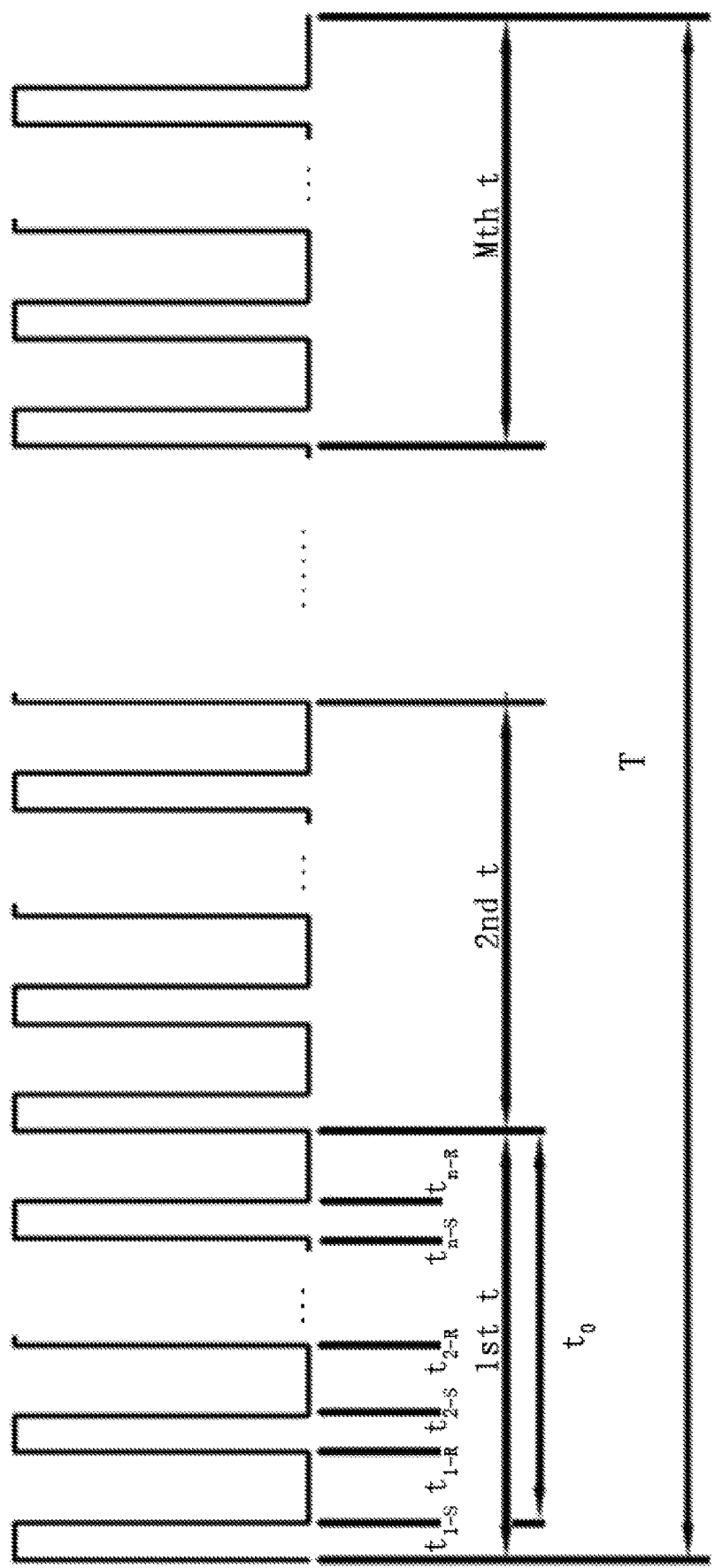
FIG. 14 is a time sequence diagram of a control method of a high-intensity focused ultrasound apparatus provided in an embodiment of the present application.

As shown in FIGS. 13 and 14, in an embodiment of the present application, the control method of a high-intensity focused ultrasound apparatus may include steps S100 to S500 as follows:

S100, sending an extending command to the transducer assembly 100 to control the transducer assembly 100 in the first shape to extend into the inner cavity of the object to be treated.

S200, sending a shape change command to the focusing transducer 120 in the transducer assembly 100 to control the focusing transducer 120 to perform a shape change from the first shape to the second shape.

S300, setting a length of time of one operating cycle t and a number n of regions to be treated in one operating cycle t. n is a positive integer and n is greater than 0.

S400, sending an operating command to the focusing transducer 120 to control the focusing transducer 120 to perform an ultrasonic pulse treatment successively on the n regions to be treated in one operating cycle t.

S500, repeatedly performing step S400 to control the focusing transducer 120 to perform ultrasonic pulse treatments on the n regions to be treated within a total operating cycle T. The total operating cycle T includes M operating cycles t. M is a positive integer and M is greater than 0.

Specifically, the processor may pre-store codes for setting a length of time of one operating cycle t and a number n of regions to be treated in one operating cycle t. Optionally, n may be 4. In the case n is 4, during one operating cycle, the processor can control the transducer assembly 100 to perform a treatment successively on the 4 regions to be treated. Since the treatment work of a region to be treated cannot be accomplished by a single treatment, M treatments are needed to accomplish the treatment work. Therefore, the focusing transducer 120 needs to be controlled to work for M operating cycles. n and M are both positive integers and are both greater than 0.

In this embodiment, by controlling the focusing transducer 120 in the transducer to perform a shape change after the transducer assembly 100 extends into the inner cavity of the object to be treated, not only can the transducer assembly 100 extend through a narrow part into the inner cavity of the object to be treated, but also normal operation requirements of the transducer assembly 100 are satisfied after extension into the inner cavity of the object to be treated. In addition, by controlling the focusing transducer 120 to perform an ultrasonic pulse treatment successively on the plurality of regions to be treated in one operating cycle, the treatment time of ultrasonic pulse treatment is saved and the treatment efficiency is greatly improved.

In an embodiment of the present application, step S400 includes steps S410 to S460 as follows;

S410, sending a pulse on command to the focusing transducer 120 to control the focusing transducer 120 to release a high-intensity focused ultrasonic pulse to irradiate a first region to be treated of the inner cavity of the object to be treated for a first irradiation time period $t_{1-S}$.

S420, sending a pulse off command to the focusing transducer 120 to control the focusing transducer 120 to stop the release of the high-intensity focused ultrasonic pulse for a first rest time period $t_{1-R}$.

S430, sending a region shift command to the focusing transducer 120 to control the focusing transducer 120 to move from one region to be treated to another region to be treated.

S440, sending a pulse on command to the focusing transducer 120 to control the focusing transducer 120 to release a high-intensity focused ultrasonic pulse to irradiate a second region to be treated of the inner cavity of the object to be treated for a second irradiation time period $t_{2-S}$.

S450, sending a pulse off command to the focusing transducer 120 to control the focusing transducer 120 to stop the release of the high-intensity focused ultrasonic pulse for a second rest time period $t_{2-R}$.

S460, repeatedly performing steps S430 to S450 until the focusing transducer 120 is controlled to accomplish irradiation of an nth region to be treated of the inner cavity of the object to be treated for an nth irradiation time period $t_{n-S}$, and controlling the focusing transducer 120 to stop the release of the high-intensity focused ultrasonic pulse for an nth rest time period $t_{n-R}$.

Specifically, it may be appreciated that the parameters in this embodiment satisfy the following formula 1:

$$T = M \lambda t = M \times (t_{1-S} + t_{1-R} + t_{2-S} + t_{2-R} + \ldots t_{n-S} + t_{n-R}) \quad \text{formula 1}$$

T is a total operating cycle. M is the number of operating cycles included in the total operating cycle. t is an operating cycle. $t_{1-S}$ is a first irradiation time period. $t_{1-R}$ is a first rest time period. $t_{2-S}$ is a second irradiation time period. $t_{2-R}$ is a second rest time period. $t_{n-S}$ is an nth irradiation time period.

$t_{n-R}$ is an nth rest time period. n is the number of regions to be treated in one operating cycle.

It is to be noted that the irradiation time periods of the pulse may be equal or unequal in the different regions to be treated. Similarly, the rest time periods in which the release of the pulse is stopped may be equal or unequal in different regions to be treated. Using an example for explanation, the first irradiation time period $t_{1-S}$ may be equal to the second irradiation time period $t_{2-S}$, and the first irradiation time period $t_{1-S}$ may also be unequal to the second irradiation time period $t_{2-S}$. The first rest time period $t_{1-R}$ may be equal to the second rest time period $t_{2-R}$, and the first rest time period $t_{1-R}$ may also be unequal to the second rest time period $t_{2-R}$.

In addition, the irradiation time period of the pulse may be equal to the rest time period in which the release of the pulse is stopped, and they may also be unequal.

In a conventional solution, in one operating cycle, a control focusing transducer 120 is controlled to irradiate only one region to be treated, and after the irradiation is finished, and all the remaining time in the operating cycle is used for rest, with a rest time of to. In this embodiment, by setting multiple sets of continuous pulse irradiation time periods and rest time periods for different regions to be treated in one operating cycle, the total treatment time for the n regions to be treated is greatly reduced, and the operating efficiency is improved. For each region to be treated, the irradiation time and the rest time in a single operating cycle in the conventional solution are equal to those in the solution in this embodiment. The number of operating cycles is equal.

The technical features of the above-described embodiments can be combined in any way. For the sake of brevity, not all possible combinations of the technical features of the above-described embodiments are described. However, as long as there are no contradictions in the combinations of the technical features, they should be considered to be within the scope of this specification.

The above-described embodiments express only several embodiments of the present application, and description thereof is relatively specific and detailed, but they should not be construed as limiting the patent scope of the present application. It should be noted that for those of ordinary skill in the art, various modifications and improvements may also be made without departing from the conception of the present application, and all these modifications and improvements should be encompassed within the protection scope of the present application. Therefore, the protection scope of the present application should be defined by the appended claims.

The invention claimed is:

1. A high-intensity focused ultrasound apparatus, comprising a transducer assembly (100) and a connecting wire (200) that are fixedly connected to each other, the connecting wire (200) comprising a connecting end (210), the connecting wire (200) being fixedly connected to the transducer assembly by means of the connecting end (210), the transducer assembly (100) comprising:

an image transducer (110) configured to acquire an ultrasonic image of an inner cavity of an object to be treated; and a focusing transducer (120) configured in a first shape, the focusing transducer (120) freely changing to a second shape after extending into the inner cavity of the object to be treated, and configured to focus ultrasonic energy and release a high-intensity focused ultrasonic pulse to irradiate a region to be treated of the inner cavity of the object to be treated;

wherein the second shape is a circular cylinder or an elliptic cylinder, at least one end face of the circular cylinder or the elliptic cylinder being a concave spherical surface; the focusing transducer (120) has a recess (121); and the image transducer (110) is in the shape of a circular cylinder or an elliptic cylinder, and the image transducer (110) is embedded in the recess (121), with a circle center of an end face of the image transducer (110) coinciding with a physical center of an end face of the focusing transducer (120);

wherein the focusing transducer (120) is consisted of two first transducer modules (124) and a second transducer module (123), the two first transducer modules (124) being arranged on two sides of the second transducer module (123) respectively and being pivotally connected to the respective side of the second transducer module (123); the recess (121) is provided at center of the second transducer module (123);

when the high-intensity focused ultrasound apparatus (10) is in a first state, the two first transducer modules (124) are folded and combined to form the focusing transducer (120) in the first shape, the first state being that the high-intensity focused ultrasound apparatus (10) is outside the object to be treated, the first shape being the shape of the second transducer module (123);

when the high-intensity focused ultrasound apparatus (10) is in a second state, the two first transducer modules (124) are unfolded and spliced to form the focusing transducer (120) in the second shape, the second state being that the high-intensity focused ultrasound apparatus (10) is adapted to be in the inner cavity of the object to be treated; and the image transducer (110) is embedded in the recess (121), and during a shape change of the focusing transducer (120), the shapes of the second transducer module (123) and the image transducer (110) remain unchanged.

\* \* \* \* \*